(12) United States Patent
Guo et al.

(10) Patent No.: US 6,503,227 B1
(45) Date of Patent: Jan. 7, 2003

(54) GUIDE WIRE BRAKE

(75) Inventors: Zihong Guo, Bellevue, WA (US); Verivada Chandrasekaran, Mercer Island, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 263 days.

(21) Appl. No.: 09/624,429

(22) Filed: Jul. 24, 2000

(51) Int. Cl.[7] ............................................... A61B 17/00
(52) U.S. Cl. ................... 604/164.07; 606/159; 606/167; 606/180
(58) Field of Search ................... 604/164.07; 606/159, 606/180, 167

(56) References Cited

U.S. PATENT DOCUMENTS

| | | |
|---|---|---|
| 4,679,557 A | 7/1987 | Opie et al. |
| 4,926,858 A | 5/1990 | Gifford, III et al. |
| 5,011,490 A | 4/1991 | Fischell et al. |
| 5,314,407 A | 5/1994 | Auth et al. |
| 5,490,859 A | 2/1996 | Mische et al. |
| 5,501,694 A | 3/1996 | Ressemann et al. |
| 5,584,843 A | 12/1996 | Wulfman et al. |
| 5,667,490 A | 9/1997 | Keith et al. |
| 5,779,722 A | 7/1998 | Shturman et al. |
| 5,893,857 A | 4/1999 | Shturman et al. |
| 6,149,663 A | * 11/2000 | Strandberg et al. ......... 600/581 |

FOREIGN PATENT DOCUMENTS

| | | |
|---|---|---|
| EP | 0 268 228 A2 | 5/1988 |
| WO | WO 99/51148 | 10/1999 |

* cited by examiner

Primary Examiner—J. Casimer Jacyna
(74) Attorney, Agent, or Firm—Christensen O'Connor Johnson Kindness PLLC

(57) ABSTRACT

An improved guide wire brake that is particularly suited to ablative rotational atherectomy devices is disclosed. The guide wire brake ensures that a guide wire is prevented from rotating or moving axially prior to activation of a primary mover such as a turbine. In one embodiment a pressure relief valve delays the activation of the prime mover on start up, and a check valve delays the release of the guide wire brake on shut down. In a second embodiment the guide wire brake is serially connected to the prime mover such that the prime mover is not connected to the pressurized gas source until after the guide wire brake is engaged. In a third embodiment a guide wire is disposed through a flexible tube within a rigid cylinder that is serially connected to the prime mover, such that when pressurized gas is provided to the prime mover the flexible tube will collapse on the guide wire, to prevent guide wire movement. In a fourth embodiment a mechanical brake, in a single action, engages the guide wire prior to opening a flow path between the pressurized gas source and the prime mover. Methods for manually bypassing the guide wire brake are also disclosed.

10 Claims, 11 Drawing Sheets

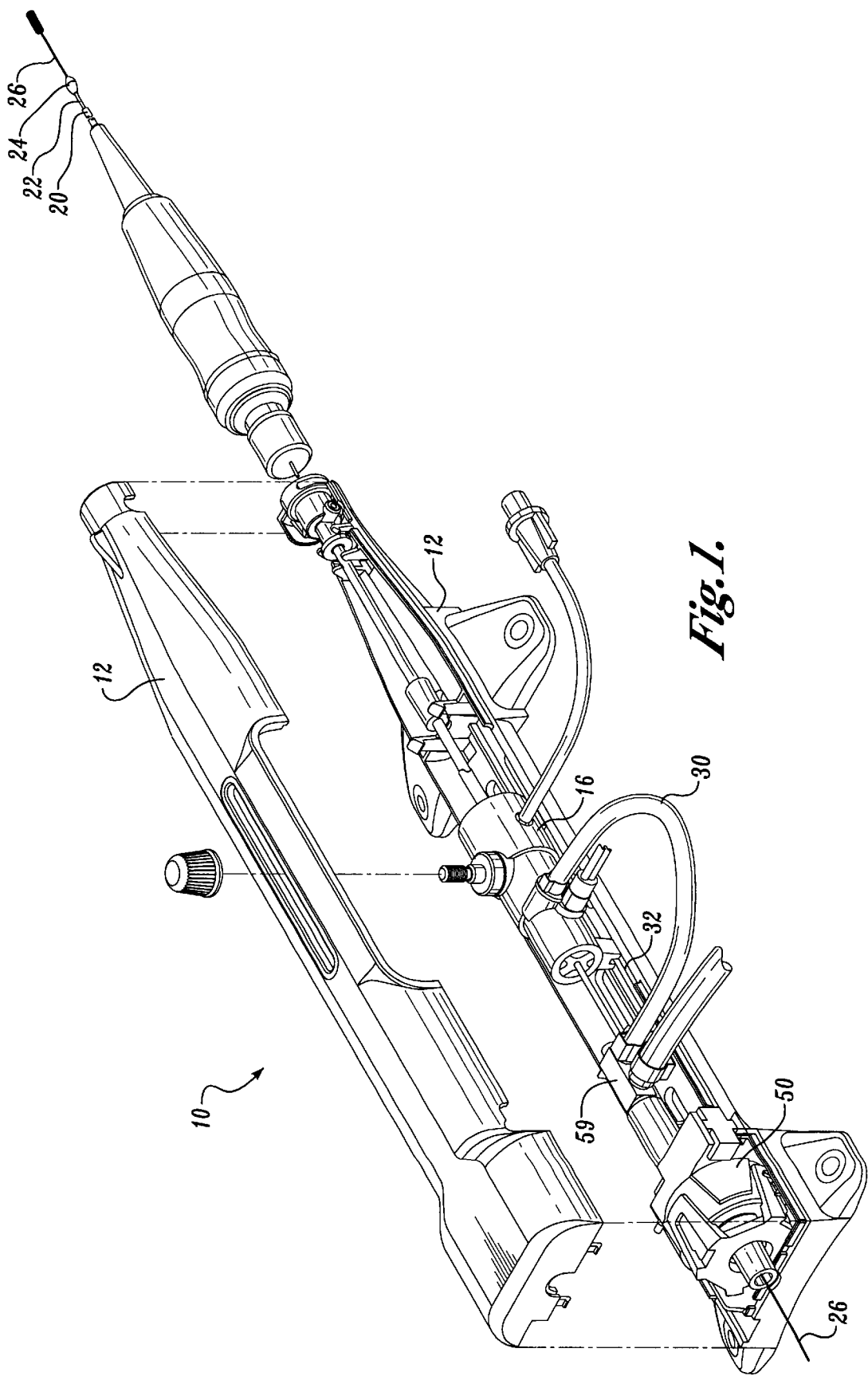

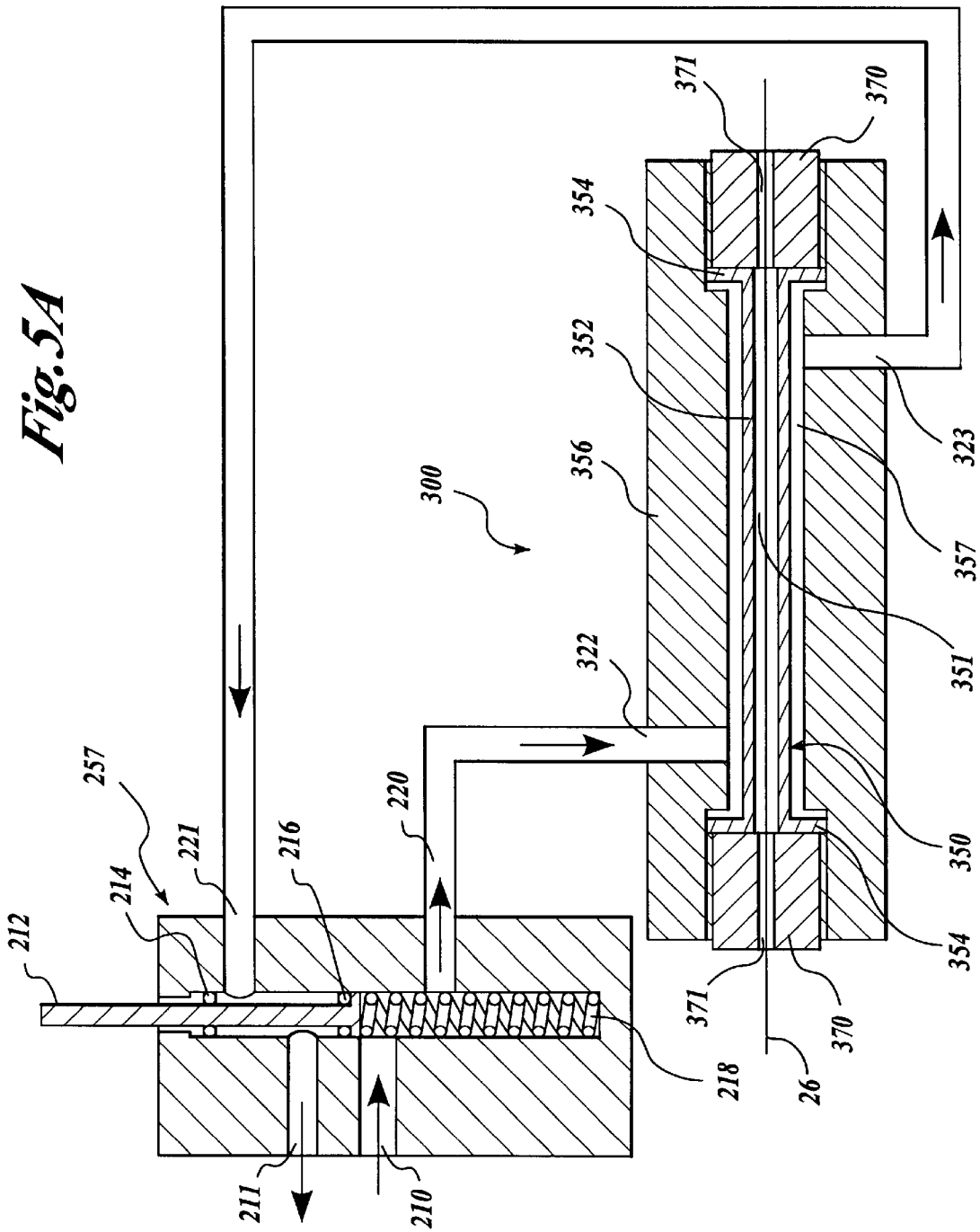

GUIDE WIRE BRAKE

FIELD OF THE INVENTION

The present invention relates to medical devices used to differentially ablate or cut deposits from within a patient's vasculature, and in particular to guide wire braking mechanisms for such medical devices.

BACKGROUND OF THE INVENTION

A variety of techniques and instruments have been developed for removing health-threatening deposits in a patient's arteries and similar body passageways. Such deposits may be caused by a number of diseases such as arteriosclerosis, a condition characterized by the buildup of deposits (atheromas) in the intimal layer of a patient's blood vessels. If the atheroma has hardened into a calcified atherosclerotic plaque, removal of the deposit can be particularly difficult. Deposits in the vasculature can restrict the flow of blood to vital organs, such as the heart or brain, and can cause angina, hypertension, myocardial infarction, strokes, and the like.

Several kinds of atherectomy devices have been developed for removing such deposits. One such device that is particularly suited to removing calcified atherosclerotic plaque, is an ablative rotational atherectomy device, such as that disclosed in U.S. Pat. No. 4,990,134 by Auth. Auth teaches using a small burr covered, or partially covered, with an abrasive cutting material, such as diamond grit. The burr is attached to the distal end of a flexible, rotatable drive shaft. A rotational atherectomy device practicing the Auth invention is sold by the assignee of the present invention under the trademark Rotablator® and is described below.

The Rotablator® ablative device 10, depicted in FIG. 1, utilizes a guide wire 26 that is inserted through the patient's body approximately to the location of the deposit that is to be treated. A hollow, flexible drive shaft 22 having an ablative burr 24 at its distal end is then inserted over the guide wire 26, and advanced to a location just proximal to the deposit. The drive shaft 22 is covered with a lumen or catheter 20 along most of its length to minimize the impact to surrounding tissue when the drive shaft 22 is rotatably engaged. The drive shaft 22 is connected to a compressed-air driven drive assembly 16 having a turbine (not shown) that can rotate the drive shaft 22 at relatively high rotational speeds, typically in the range of, e.g., about 150,000 to about 190,000 rpm. The drive assembly 16 is slidably mounted in an advancer housing 12 on a track 32, allowing a surgeon using the device 10 to move the drive assembly 16 transversely, and hence move the drive shaft 22 and burr 24 forward and backward to ablate the atheroma. When the turbine is engaged, that is, when compressed air is being supplied to the drive assembly 16, a guide wire brake 50 normally clamps onto the guide wire 26, preventing the guide wire 26 from rotating or moving laterally while the drive shaft 22 is rotating.

A prior-art guide wire brake 50 for an ablative rotational atherectomy device is shown in FIG. 2A. This prior art guide wire brake 50 comprises a brake collet 52 axially supported in a brake cylinder 56 containing a free piston 54 with a lip seal 55. The guide wire 26 runs axially through the collet 52, cylinder 56, and piston 54. As seen most clearly in FIG. 2B, the brake collet 52 is an elongate member having an upper portion 41 disposed opposite an identical lower portion 42. The upper and lower portions 41, 42 are separated by a narrow gap 47 along most of the length of the brake collet 52. The brake collet 52 has a tubular back portion 45 and a head portion 46 wherein the head portion 46 upper and lower portions 41, 42 generally form a pair of abutting truncated cones that are coaxial with the back portion 45. The gap 47 separating the upper portion 41 from the lower portion 42 extends entirely through the head portion and most of the way through the back portion 45, wherein interior flat faces 49 on the upper and lower portions 41, 42 are disposed on either side of the gap 47. A narrow strip of the back portion 45 connects the upper portion 41 to the lower portion 42, elastically biasing the upper portion 41 and lower portion 42 in an "unclamped" position wherein the gap is wider than the diameter of the guide wire 26.

As shown in FIG. 2A, the piston 54 has a collet engagement orifice 48 that slidably engages the head portion 46 of the collet 52 at the gapped end. Because the head portion 46 is conically tapered, urging the collet engagement orifice 48 axial against the head portion 46 will deflect the upper and lower portions 41, 42 of the collet 52 toward each other, into a closed or clamped position. A spring 53 fits over the brake collet 52 and biases the piston 54 away from the collet 52. During ablation, the compressed air that powers the drive assembly 16 enters the Rotablator® 10 via a manifold 59 having a first outlet port 61 fluidly connected to the brake cylinder 56, and a second outlet port 62 leading to the drive assembly 16 through tube 30. When compressed air is provided to the drive assembly 16 it is supplied in parallel to the brake cylinder 56. The piston 54 is thereby urged distally toward the brake collet 52, causing the collet engagement orifice 48 to elastically compress the head portion 46 around the guide wire 26 when the turbine is engaged.

Under certain circumstances, it is desirable to override the guide wire brake 50 and release the guide wire 26 even when the turbine and the drive shaft 22 are rotating. For example, it is sometimes desirable to engage the turbine when the drive shaft 22 is advanced over the guide wire 26 to the target position within an artery, or when the drive shaft 22 is being removed from the artery. Sometimes it is also useful to override the guide wire brake to permit advancement or retraction of the guide wire 26 within the rotating drive shaft 22. The Rotablator® provides a "dynaglide" mode wherein the guide wire 26 is enclamped when turbine is operated at a lower velocity in order to facilitate such drive shaft insertion and removal. For these and other situations, a bypass valve 57 is provided between the manifold 59 and the brake cylinder 56, whereby the first manifold outlet 61 to the brake cylinder 56 may be closed. This allows the pressurized gas to drive the turbine without engaging the guide wire brake 50.

An alternative guide wire brake for an atherectomy device is disclosed in U.S. Pat. No. 5,779,722 to Shturman et al., wherein a mechanical guide wire brake is coupled to a mechanical turbine brake. Shturman et al. teaches a mechanical system wherein translation of the turbine along its track, (which is generally performed to move the burr back and forth over the atheroma), has a range of positions that will engage a turbine brake, and a further range that will then release the guide wire brake. A separate override clamp may be secured to the device to release the guide wire brake without engaging the turbine brake. While the device disclosed by Shturman et al. provides an alternate method of ensuring the guide wire brake is engaged when the turbine is operated, the device has the disadvantages of being relatively complicated to build and to operate. In addition, it is possible that the override clamp could be inadvertently left in place, whereby the guide wire could undesirably be free to move.

It is desirable to provide a guide wire brake assembly that ensures that automatically resets any brake override or bypass mechanisms when the drive assembly is engaged. It is further desirable to have a guide wire brake that engages more quickly or earlier than the turbine when the compressed air supply is switched on, and disengages more slowly or later than the turbine, when the compressed air supply is switched off. It is further desirable to provide a guide wire brake that is mechanically simple and easy to operate.

SUMMARY OF THE INVENTION

A novel guide wire brake particularly suited to ablative rotational atherectomy devices is disclosed. Ablative rotational atherectomy is a procedure for removing unhealthy deposits within a body by inserting an ablative burr proximate a deposit, and rotating the burr to remove the deposit. A fine guide wire is first inserted, typically through the patient's vasculature, to the deposit site. A flexible, tubular drive shaft, with the ablative burr at its distal end, is then inserted over the guide wire and guided to the proper location. A catheter covers the drive shaft along most of its length to minimize the impact to local tissues. In normal operation, the guide wire is then clamped at its proximal end to prevent axial or rotational motion, and a prime mover, such as a turbine, is engaged to rotate the drive shaft and burr. The guide wire brake of the present invention clamps the guide wire prior to the activation of the prime mover, and slightly delays the release of the clamp to allow the rotational inertia of the prime mover to dissipate prior to unclamping the guide wire.

In one embodiment the guide wire brake is connected in parallel to a pressurized gas source that drives the prime mover and utilizes a piston in a cylinder to activate the guide wire brake. A pressure relief valve is provided between the pressurized gas source and the prime mover that has an activation pressure greater than the guide wire brake activation pressure, whereby the guide wire brake will engage the guide wire prior to the pressure relief valve opening to the prime mover. Additionally, a check valve is connected to the guide wire brake cylinder that prevents or impedes the flow of gas out of the brake cylinder, thereby delaying the release of the guide wire brake after the pressurized gas source is disconnected or turned off.

In another embodiment of the invention a pneumatic guide wire brake is connected in series between the pressurized gas source and the prime mover. The guide wire brake cylinder includes a side outlet port that leads to the prime mover, whereby the side outlet port does not open until after the guide wire brake has been engaged.

In yet another embodiment of the present invention, a pneumatic guide wire brake is connected in series between the pressurized gas source and the prime mover. The guide wire brake consists of a flexible tube through which the guide wire passes that is suspended within a rigid cylinder. When the pressurized gas passes through the rigid cylinder prior, the increased pressure causes the flexible tube to collapse around the guide wire, thereby clamping the guide wire.

In still another embodiment of the present invention, a mechanically-engaged guide wire brake is provided, wherein rotation of a valve to a first position will engage the guide wire break prior to opening a channel between the pressurized gas source and the prime mover.

In each of the embodiments disclosed herein an optional valve is provided whereby the guide wire brake can be selectively bypassed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a partially exploded isometric view of a prior art rotational ablation device;

FIG. 5A is a schematic representation of a third embodiment of a guide wire brake of the present invention with a bypass valve in an open position;

DETAILED DESCRIPTION OF THE PREFERRED EMBODIMENT

Figure 2A:
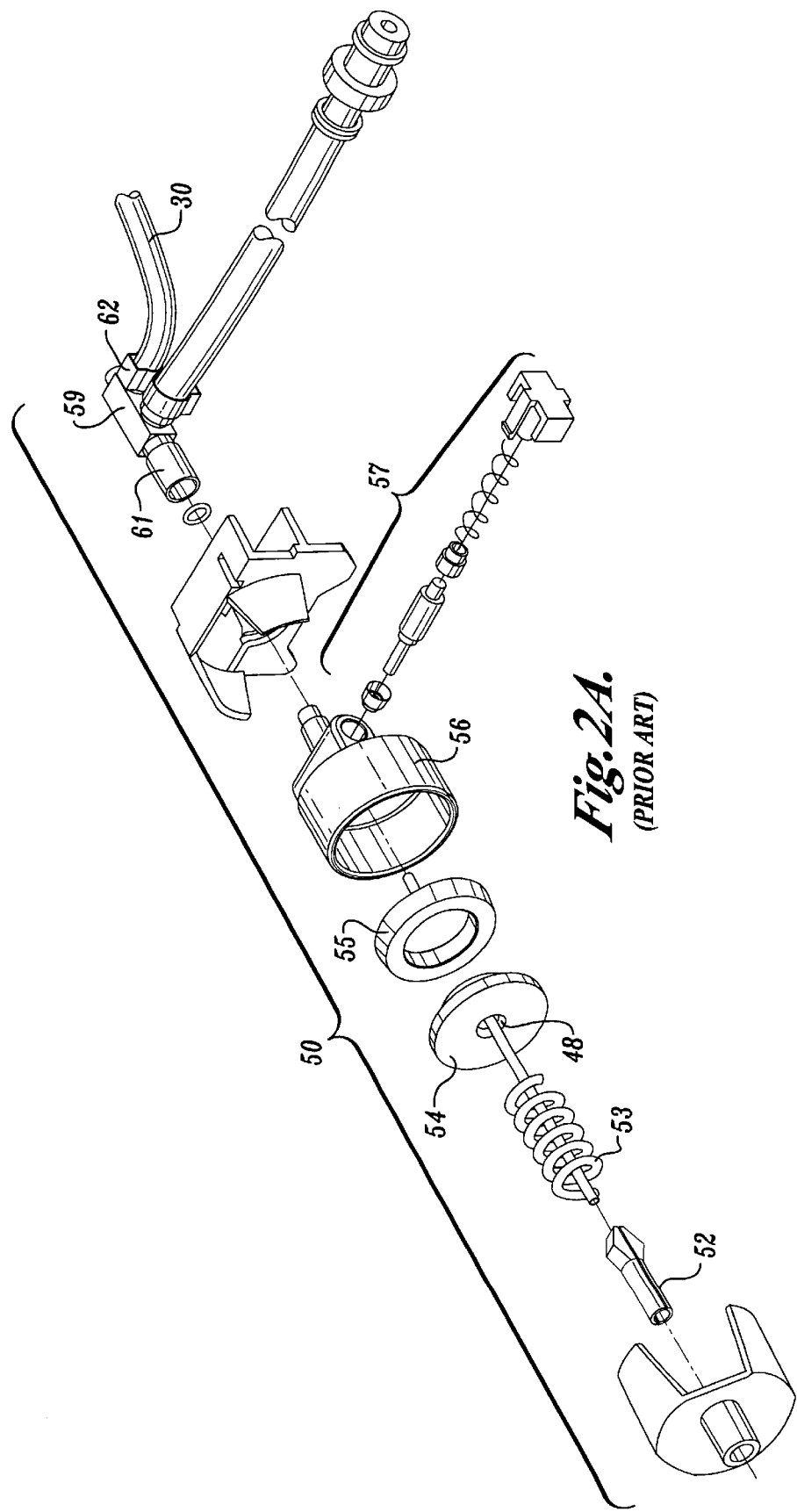
FIG. 2A is an exploded isometric view of a prior art guide wire brake assembly.
Figure 2B:
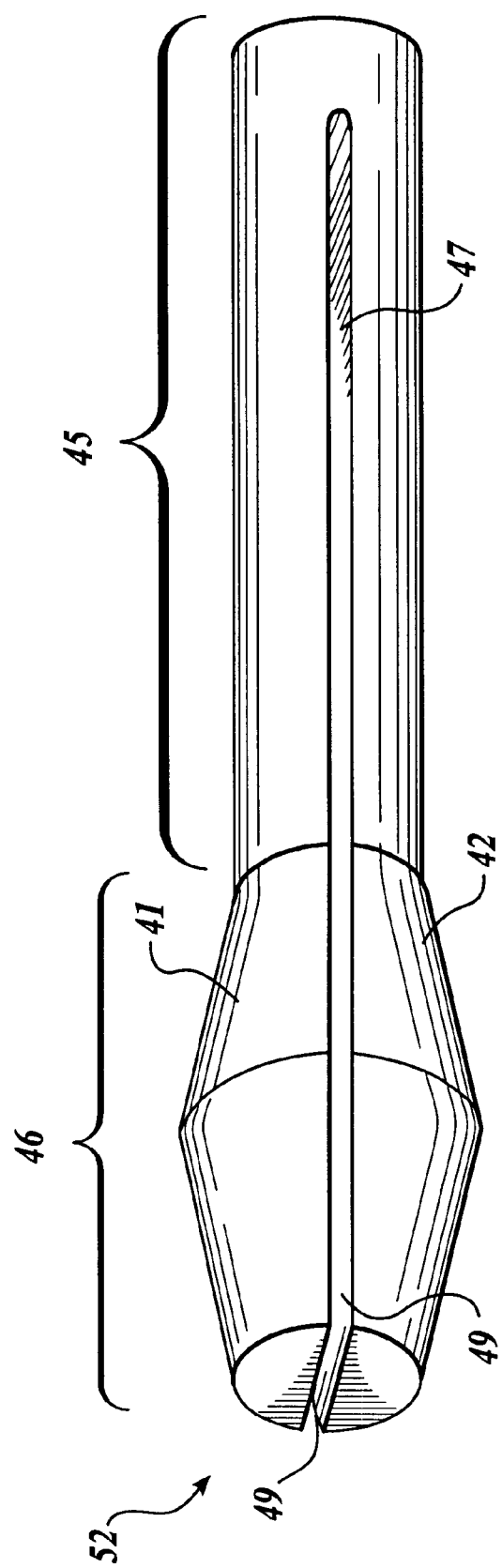
FIG. 2B is an isometric view of a prior art brake collect.

As discussed above, FIG. 1 shows a rotational ablation device 10, illustrating the application for which the present invention was developed. Although the present invention will be illustrated with respect to a rotational ablation device 10, it is contemplated that the invention will find other applications as well.

The ablation assembly 10 includes ablation burr 24 attached to the distal end of drive shaft 22. The drive shaft 22 is coupled to a drive assembly 16 having a compressed-gas-driven turbine (not shown). The drive assembly 16 is slidably mounted on a single-rail track 32, whereby the drive assembly 16 can be selectively moved longitudinally. The drive assembly 16 transmits torque to the drive shaft 22 and ablation burr 24. Given the coupling of the drive shaft 22 to the drive assembly 16, it will be appreciated that longitudinal motion of the drive assembly 16 will cause the ablation burr 24 to advance and retract, whereby the ablation burr 24 can be maneuvered through an atheroma in a patient's vasculature.

The ablation burr 24 is positioned in a patient's vasculature over the guide wire 26. The proximal end of guide wire 26 extends longitudinally through the ablation assembly 10. To limit undesired movement of the guide wire 26 during the atherectomy procedure, a guide wire brake 50 is provided, through which the guide wire 26 passes. A prior art guide wire brake 50 is depicted in FIG. 2A, and has been described above.

Figure 3A:
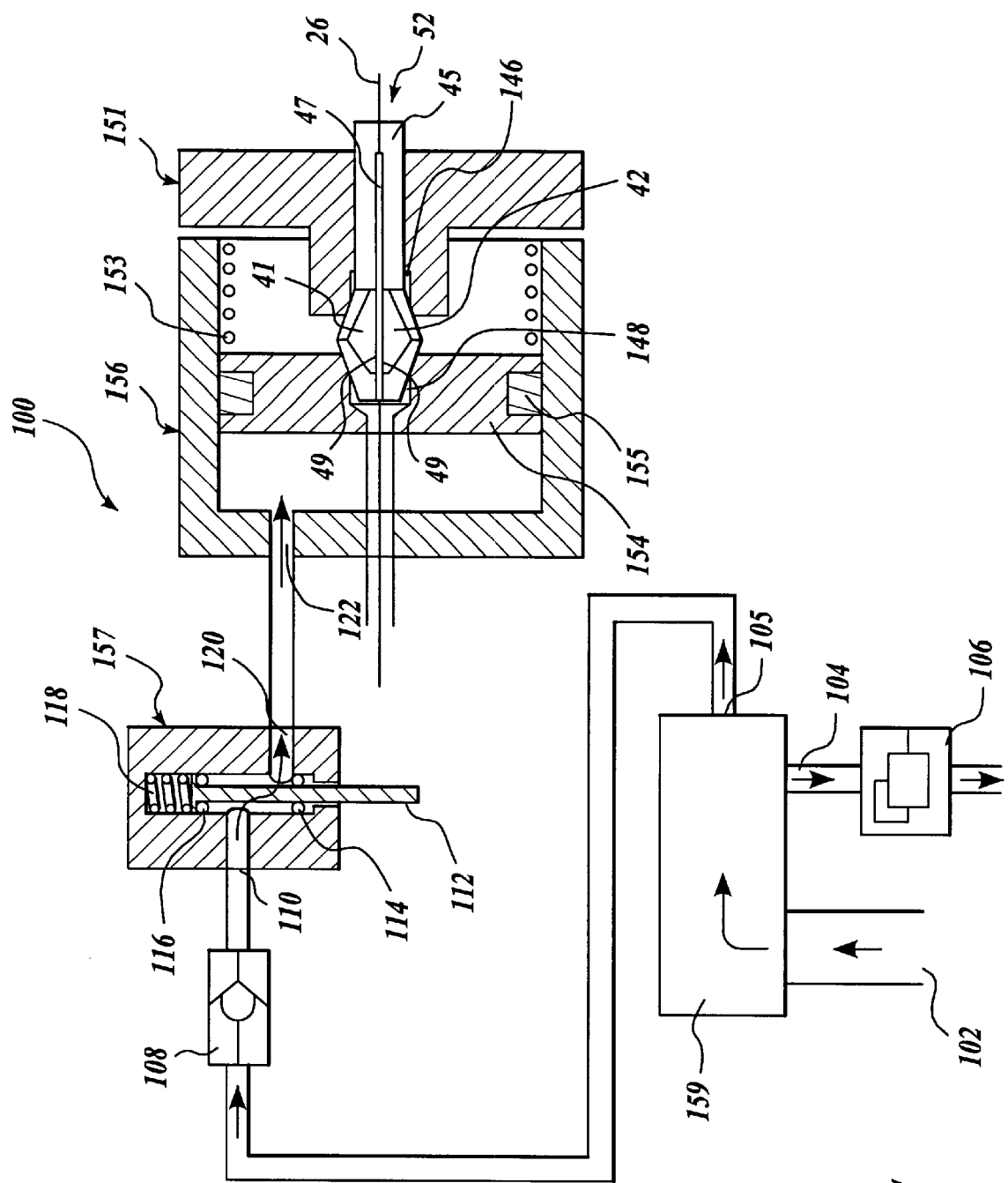
FIG. 3A is a schematic representation of a first embodiment of the guide wire brake of the present invention showing a bypass valve in an open position.
Figure 3B:
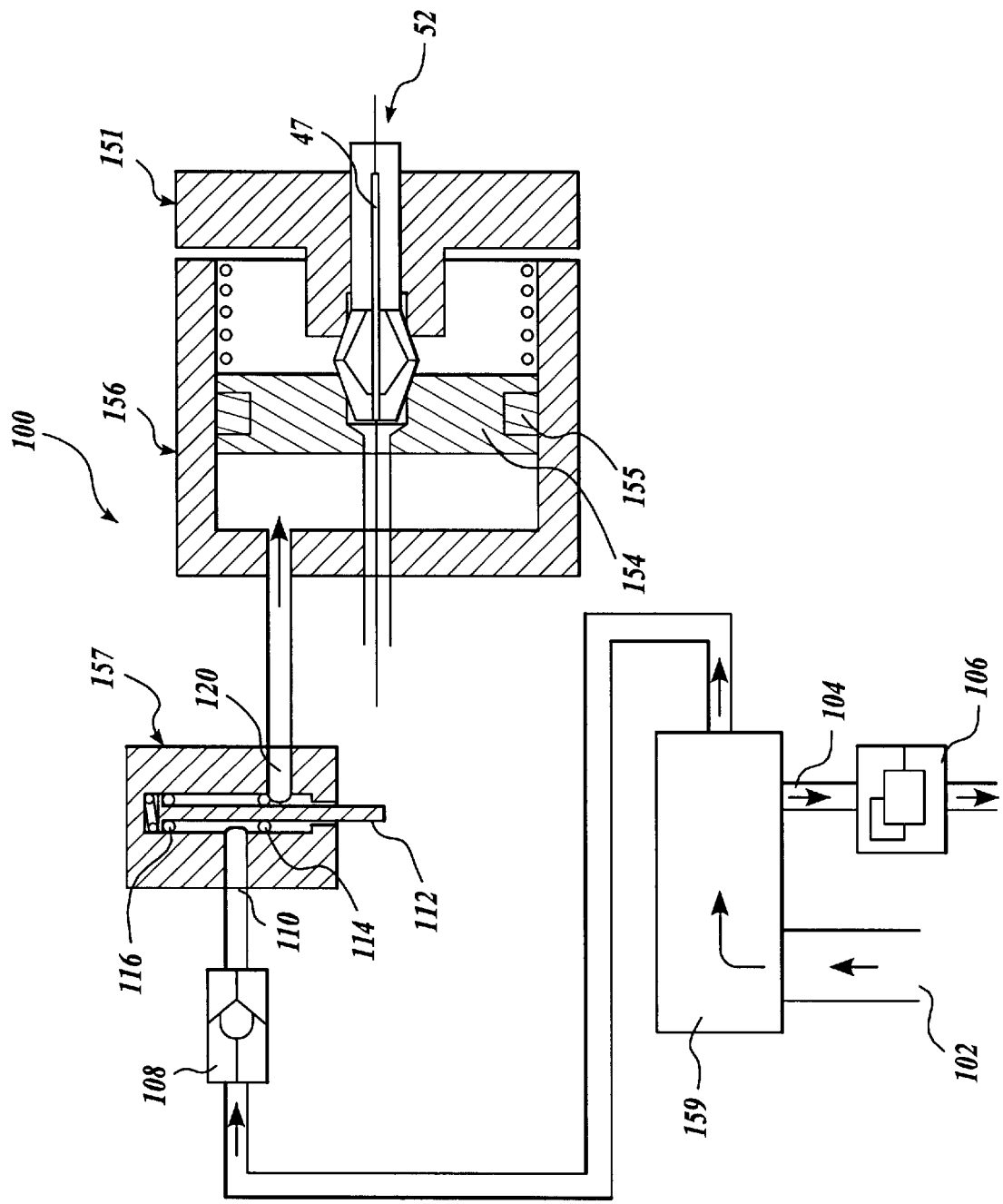
FIG. 3B is a schematic representation of the guide wire brake shown in FIG. 3A showing the bypass valve in a closed position.

A schematic view of an improved guide wire brake 100 in accordance with one embodiment of the present invention is shown in FIGS. 3A and 3B. Pressurized gas, such as air, is provided through an inlet port 102 to a manifold 159. The manifold 159 has two outlet ports 104 and 105. The outlet port 104 is connected to a pressure relief valve 106. When the pressure is sufficiently high to open the pressure relief valve 106, compressed air flows through the pressure relief valve 106 to a turbine (not shown). The second outlet port 105 fluidly connects the manifold 159 to a check valve 108, which in turn is fluidly connected to a bypass valve 157. When the bypass valve 157 is in an open position, as shown in FIG. 3A, the pressurized air flows through an input port 110 and an outlet port 120. The outlet port 120 is fluidly connected to an inlet port 122 of a brake cylinder 156. A pair of O-rings 114, 116 on a bypass button 112 seal the bypass valve 157. A spring 118 biases the valve 157 in an open position such that the inlet port 110 and outlet port 120 are fluidly connected. Pressing the bypass button 112 compresses the spring 118 and moves the O-ring 114 such that the outlet port 120 and inlet port 110 are on opposite sides of the O-ring 114 thereby closing the valve 157.

The brake cylinder 156 includes a free piston 154 that moves within the brake cylinder 156. An O-ring 155 is attached to the piston 154 to provide a seal between the interior of brake cylinder 156 and the piston 154. A top surface of the piston 154 is in fluid communication with the inlet port 122. A rear surface of the piston 154 is biased by a spring 153 away from a cylinder base 151 that closes the brake cylinder 156. The brake cylinder 156 and the piston 154 have a central hole through which a guide wire 26 is passed. A sleeve 158 is secured to the top surface of the piston 154 and extends out of the brake cylinder 156 to seal the hole through which the guide wire extends. Surrounding the hole for the guide wire 26 on the rear surface of the piston 154 is a collet engagement orifice 148.

The cylinder base 151 includes a collet support channel 146 into which the brake collet 52 is slidably disposed. The brake collet 52 has a tubular back portion 45 that fits within the collet support channel 146. The head portion 46 of the brake collet 52 has a tapered upper portion 41 and a tapered lower portion 42. The tapered upper and lower portions 41, 42 have oppositely disposed, generally parallel flat faces 49 that are separated by a gap 47 that is larger than the diameter of the guide wire 26. The back portion of collet 52 connects the upper and lower portions 41, 42, whereby the upper and lower portions can be elastically displaced towards each other.

In the unpressurized condition, a spring 153 disposed within brake cylinder 156 biases the piston 154 away from the brake collet 52, such that the brake collet 52 will not engage the guide wire 26. When pressurized gas is provided at the manifold inlet port 102 and the bypass valve 157 is in the open position, the brake cylinder 156 is fluidly connected to the pressurized gas source. The pressure in the brake cylinder 156 produces a force on the piston 154 sufficient to overcome the biasing force of the spring 153, causing the collet engagement orifice 148 to engage the tapered upper and lower portions 41, 42 of the brake collet 52, thereby urging the tapered portions 41, 42 toward each other, such that the flat faces 49 will clamp onto the guide wire 26.

The pressure relief valve 106 has an activation pressure greater than the pressure required to engage the guide wire brake 100, whereby the guide wire brake 100 will engage the guide wire 26 prior to spin-up of the turbine. It will be appreciated that when the pressurized gas source is removed, the check valve 108, in combination with the O-ring 155, inhibits the flow of gas out of the brake cylinder 156, and will substantially seal the interior of the brake cylinder 156. The substantially sealed volume in the brake cylinder 156 will therefore maintain a positive pressure for a period of time, thereby delaying release of the guide wire brake 100. In prototype tests, the release of the guide wire brake 100 has been found to occur approximately one second after the pressurized gas is shut off, which is approximately four times longer than the release time of the prior art guide wire brake 10 described above.

FIG. 3B shows a schematic of the first preferred embodiment of the guide wire brake 100 shown in FIG. 3A, with the bypass valve 157 in a closed position. When the bypass valve 157 is closed by depressing the bypass valve button 112, the bypass O-ring 114 is moved past the outlet port 120, so that the guide wire brake 100 is fluidly disconnected from the inlet port 110. Therefore the brake cylinder 156 is no longer fluidly connected to the manifold 159, and the pressurized gas entering the inlet port 102 will drive the turbine without engaging the guide wire brake 100. It will be appreciated that a constant pressure must be applied to the bypass valve button 112 to overcome the biasing force from the spring 118, in order to bypass the guide wire brake 100.

Figure 4A:
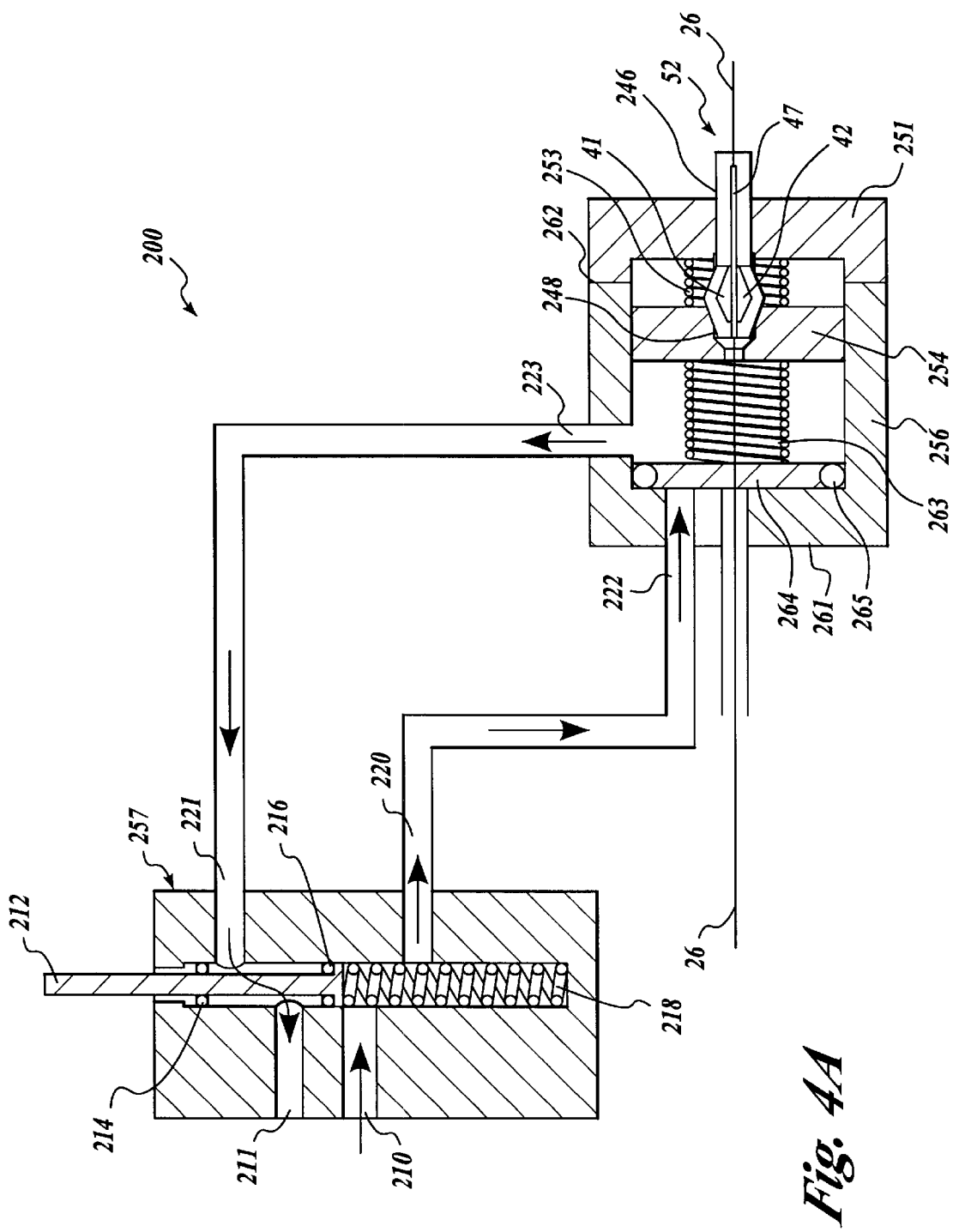
FIG. 4A is a schematic representation of a second embodiment of a guide wire brake of the present invention with no pressurized gas supplied to the guide wire brake.
Figure 4B:
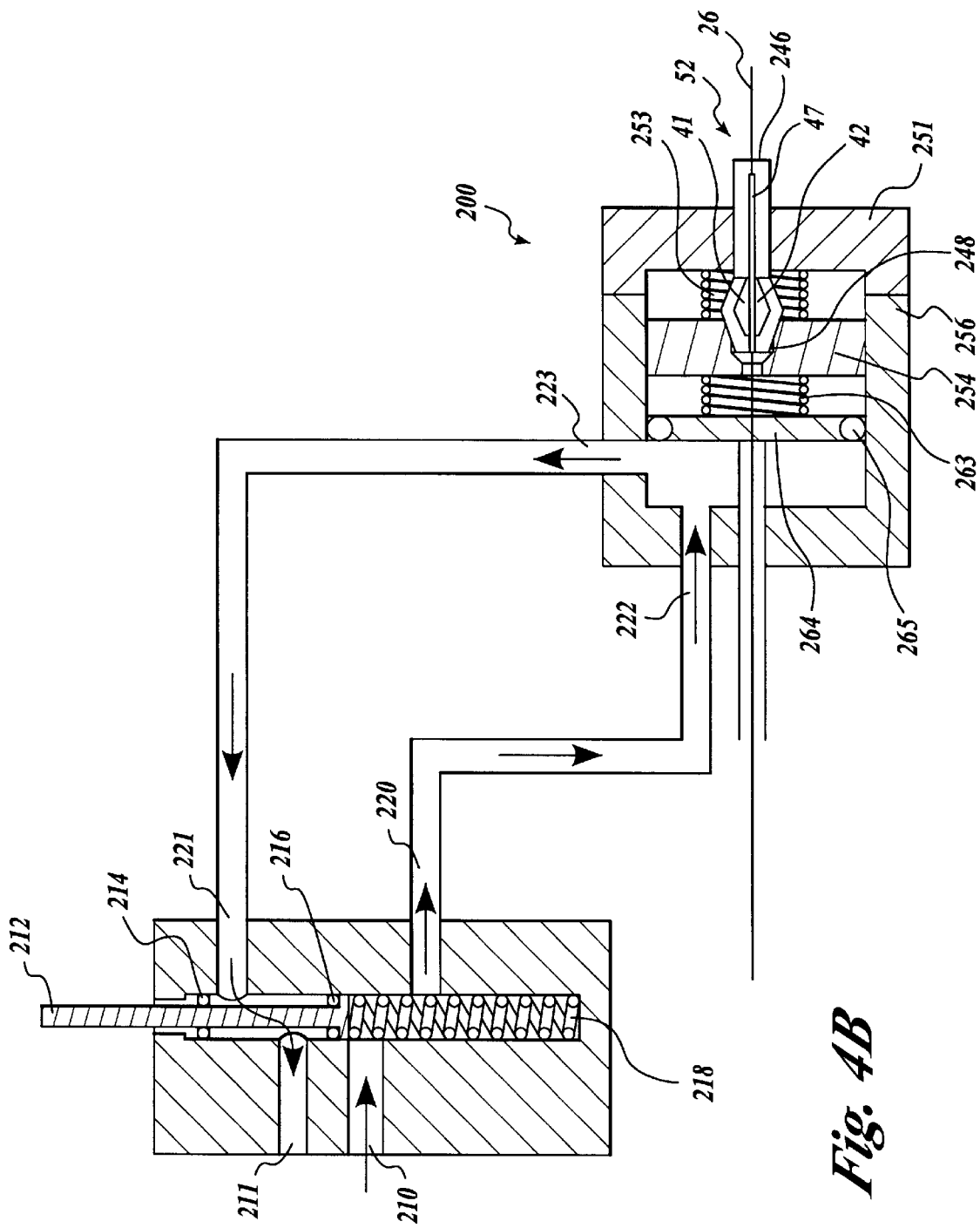
FIG. 4B is a schematic representation of the guide wire brake shown in FIG. 4A with pressurized gas supplied to the guide wire brake and with a bypass valve is in an open position.
Figure 4C:
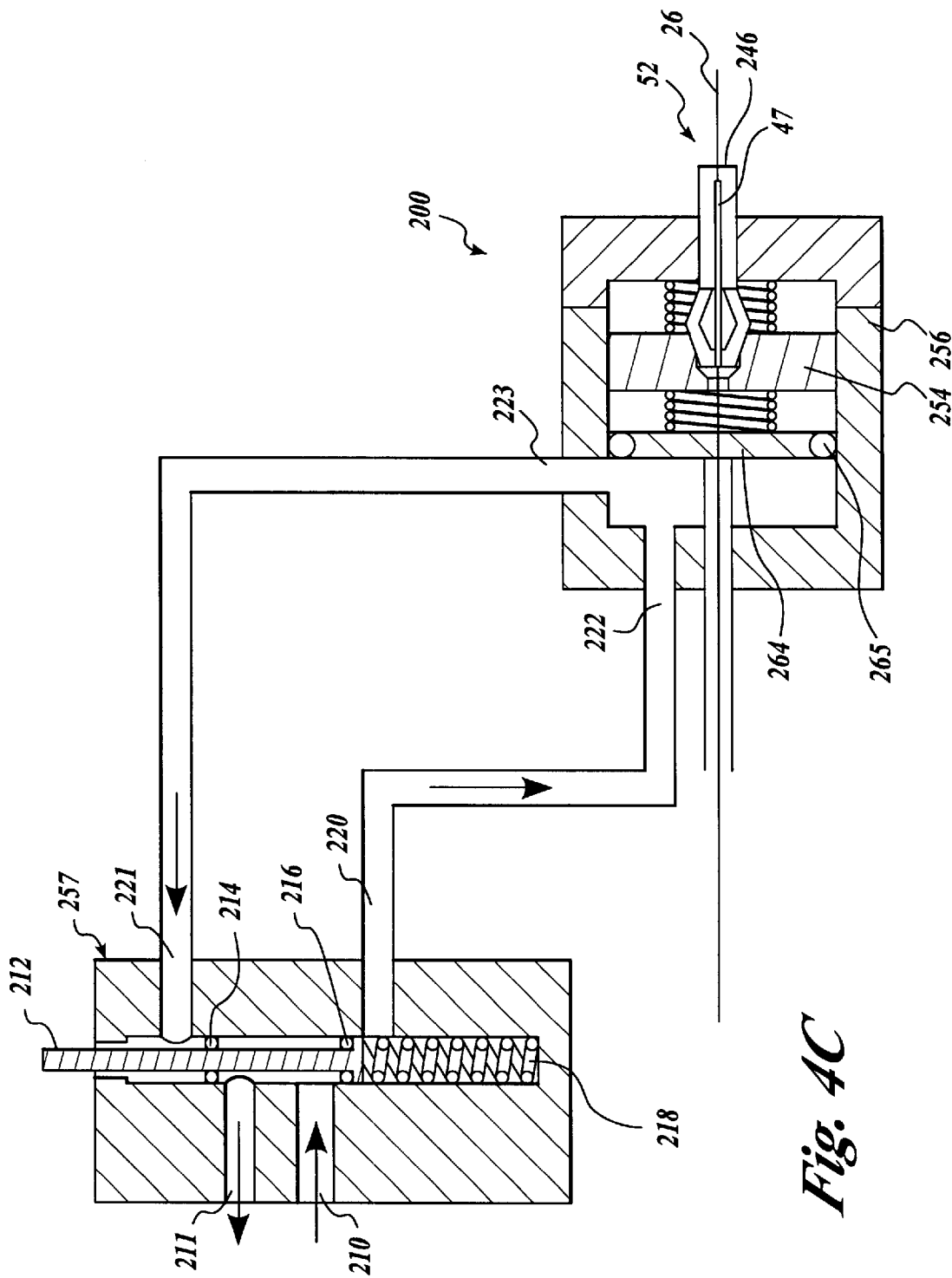
FIG. 4C is a schematic representation of the guide wire brake shown in FIG. 4A with pressurized gas supplied to the guide wire brake and with the bypass valve in a closed position.

A schematic view of a second embodiment of a guide wire brake of the present invention is shown in FIGS. 4A, 4B, and 4C. In this embodiment the guide wire brake 200 is connected in series between a pressurized gas source (not shown) and a turbine (also not shown). To activate the guide wire brake 200, pressurized gas is applied to a bypass valve 257. The valve 257 has a first inlet port 210 and a first outlet port 220. The bypass valve 257 also has a second inlet port 221 and a second outlet port 211. When the bypass valve 257 is in the open position, the first inlet port 210 is fluidly connected to the first outlet port 220 and the second inlet port 221 is fluidly connected to the second outlet port 211. A push button 212 has a pair of O-rings 214, 216 that open and close the valve. A spring 218 biases the push button 212 so that the valve 257 is normally open. The first inlet port 210 is connected to a source of compressed air and the second outlet port 211 is connected to a turbine. A brake cylinder 256 is connected in series between the first outlet port 220 and the second inlet port 221. The brake cylinder 256 has a front end 261 and a back end 262. An inlet port 222 extends through the front end 261. An outlet port 223 is provided in the cylinder 256, located between the front end 261 and the back end 262.

A master piston 264 is disposed inside the cylinder 256, and is biased toward the front end 261 with a spring 263. A secondary piston 254 is also disposed in the brake cylinder 256 and is biased toward the back end 262 by the same spring 263. A cylinder base 251 closes the back end 262 of the cylinder 256. The secondary piston 254 is biased toward the brake cylinder front end 261 with a second spring 253, located between the secondary piston 254 and the cylinder base 251. A guide wire 26 extends through a hole in the secondary piston 254, the master piston 264, and the front end 261 of the brake cylinder 256. The secondary piston 254 includes a collet engagement orifice 248 on its rear surface surrounding the hole through which the guide wire 26 passes. A brake collet 52, identical to the brake collet described above, projects into the brake cylinder 256, and is supported by a collet support channel 246 in the cylinder base 251. The spring 263 and the second spring 253 are selected such that when no pressurized gas is provided at the inlet port 222, as shown in FIG. 4A, the master piston 264 is disposed adjacent the brake cylinder front end 261 and the secondary piston 254 is disposed between the brake cylinder back end 262 and the outlet port 223, so that the collet engagement orifice 248 does not engage the tapered upper and lower portions 41, 42 of the brake collet 52. The outlet port 223 is fluidly connected to a second inlet port 221 on the bypass valve 257.

As seen most clearly in FIG. 4A, before a pressurized gas is supplied at the first inlet port 210, the master piston 264 separates the brake cylinder inlet port 222 from the brake cylinder outlet port 223. In operation as shown in FIG. 4B, a pressurized gas source is fluidly connected to the first inlet port 210 which is in turn fluidly connected to the brake cylinder 256 through the first outlet port 220 of the bypass valve and the inlet port 222 of the brake cylinder. Initially the fluid path to the turbine is blocked by the master piston 264. The pressurized gas will cause the master piston 264 to move toward the brake cylinder back end 262, thereby urging the secondary piston 254 toward the brake collet 52 causing the brake collet 52 to clamp the guide wire 26. The displacement of the master piston 264 past the outlet port 223 also opens the fluid path between the pressurized gas and the turbine, through the bypass valve second inlet port 221 and second outlet port 211. It will be appreciated that the guide wire brake 200 and turbine are therefore connected in series, and the guide wire brake 200 will engage the guide wire 26 prior to spin-up of the turbine.

As seen most clearly in FIG. 4C, closing the bypass valve 257 by pressing the bypass button 212 fluidly connects the bypass valve first inlet port 210 to the second outlet port 211, thereby fluidly connecting the turbine to the pressurized gas source without engaging the guide wire brake 200. When the bypass button 212 is depressed against the biasing force of the spring 218, the bypass valve O-rings 214, 216 are moved such that the first inlet port 210 and the second outlet port 211 lie between the O-rings 214, 216 and the first outlet port 220 and the second inlet port 221 lie on opposite sides of the O-rings 214, 216, so that the pressurized gas entering the bypass valve first inlet port 210 is channeled directly to second outlet port 211 to the turbine. As with the first embodiment described above, when the pressure on the bypass valve button 212 is released, the spring 218 will return the bypass valve 257 to an open position and the serial connection to the guide wire brake 200 will be reestablished whereby the guide wire brake 200 will engage the guide wire 26.

Figure 5D:
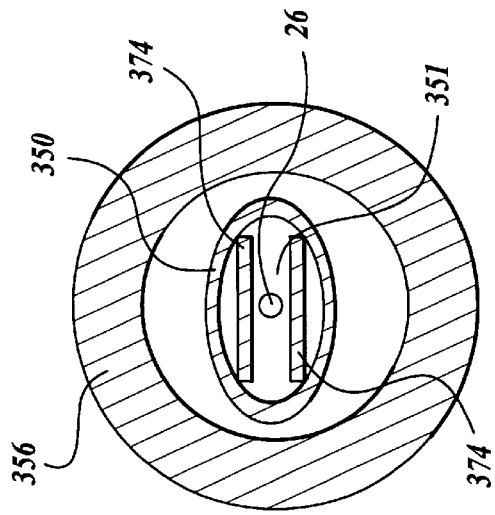
FIG. 5D is a cross-sectional view of a modified guide wire brake embodiment similar to that shown in FIG. 5A but having brake shoes inserted into an elastic brake tube.
Figure 5C:
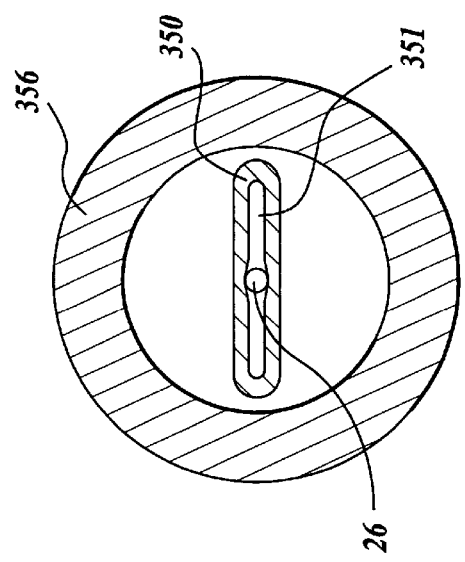
FIG. 5C is a cross-sectional view of the guide wire brake shown in FIG. 5A with the guide wire clamped.
Figure 5B:
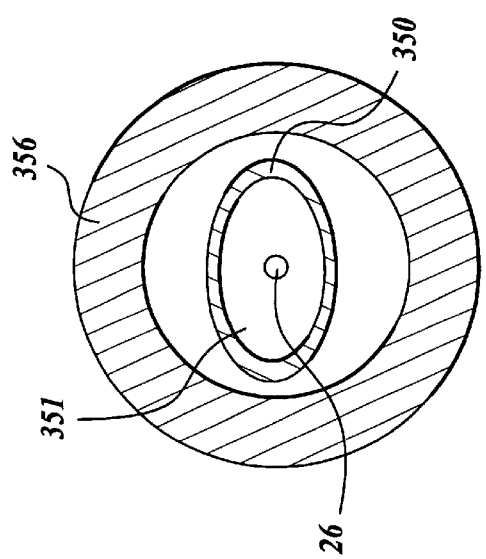
FIG. 5B is a cross-sectional view of the guide wire brake shown in FIG. 5A with the guide wire unclamped.

A third embodiment of the guide wire brake according to the present invention is shown schematically in FIGS. 5A, 5B, 5C, and 5D. This third guide wire brake 300 embodiment comprises an elastomeric brake tube 350 with an axial channel 351 therethrough, disposed in a brake cylinder cavity 352 of a brake cylinder 356. An annular transverse flange 354 extends outwardly from each end of the brake tube 350. As seen most clearly in FIG. 5B, the brake tube 350 is preferably generally elliptical or eye-shaped in cross-section. The brake tube 350 is attached to the brake cylinder 356 with a pair of threaded plugs 370 that are installed at either end of the brake cylinder cavity 352. The plugs 370 have axial orifices 371 therethrough having a diameter greater than the diameter of the guide wire 26. The guide wire 26 runs axially through the brake tube 350 and through axial orifices 371 in the plugs 370. A bypass valve 257, identical to the bypass valve described above and shown in FIGS. 4A, 4B and 4C, is provided as shown in FIG. 5A. The first outlet port 220 of the bypass valve is connected to an inlet port 322 of the brake cylinder 352. An outlet port 323 of the brake cylinder 352 is coupled to the second inlet port 221 of the bypass valve 257. As described in detail above, depressing the bypass valve button 212 against the biasing force of the spring 218 fluidly connects the bypass valve inlet port 210 to the second outlet port 211, thereby fluidly connecting the turbine to the pressurized gas source without engaging the guide wire brake 300.

In operation, a pressurized gas source is fluidly connected to the first inlet port 210 of the bypass valve 257, and thereby to the cylinder cavity 352 through the outlet ports 220 and an inlet port 322. The elastomeric brake tube 350 is a flexible member and the axial channel 351 therethrough is connected to atmospheric pressure through the plug axial orifices 371. Therefore, when the pressure in the cylinder cavity 352 is increased, the elastomeric tube 350 will collapse, thereby clamping onto the guide wire 26 disposed therethrough, as seen most clearly in FIG. 5C. The pressurized gas is fluidly connected to the turbine in series with the guide wire brake 300 through the outlet port 323 and the bypass valve 257 via the second inlet port 221 and the second outlet port 211. The guide wire brake 300 will therefore engage the guide wire 26 prior to the pressurized gas spinning up the turbine. Brake shoes 374 may optionally be inserted in brake tube 350, as shown in FIG. 5D, to alter the clamping characteristics of the guide wire brake 300.

Figure 6:
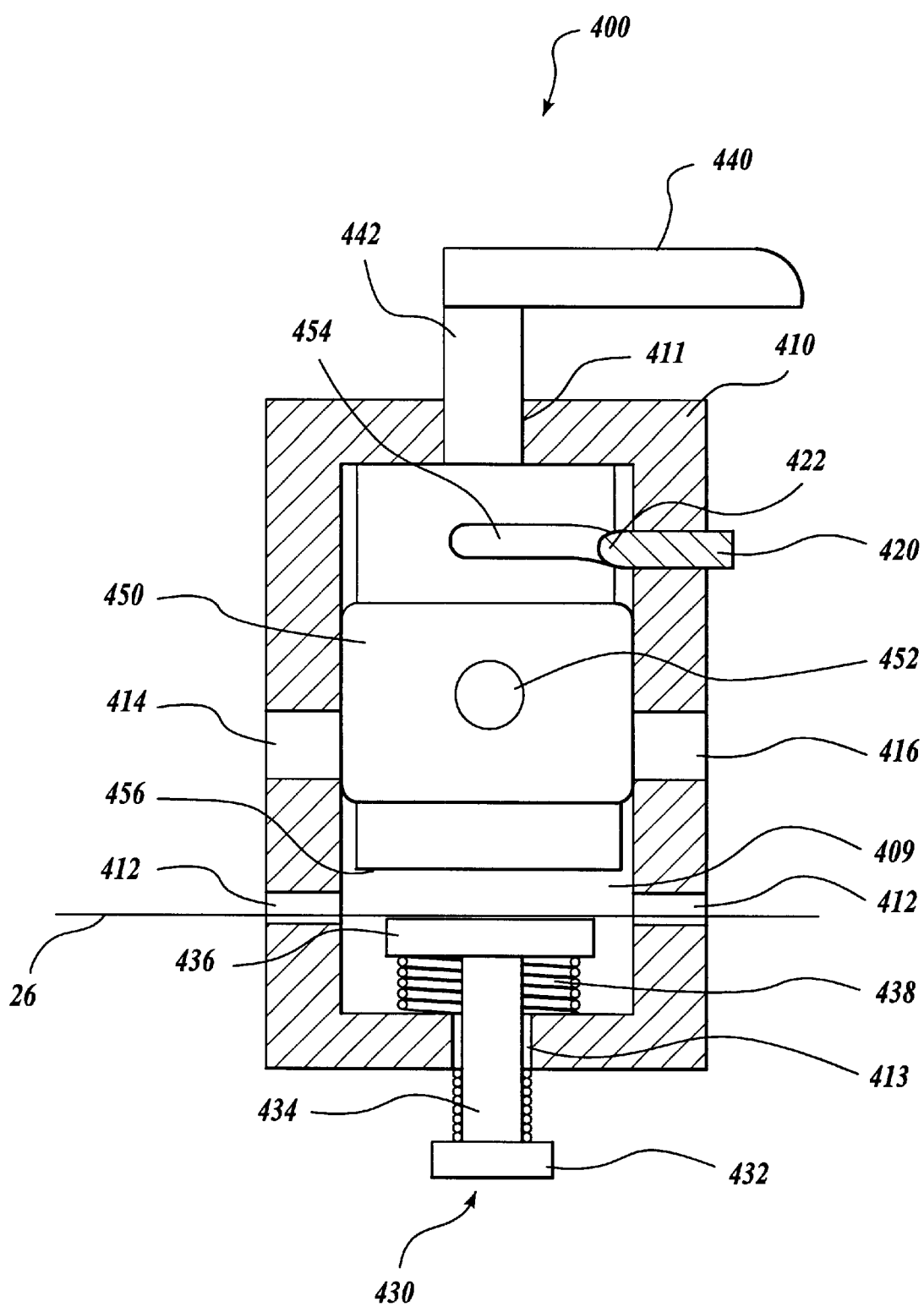
FIG. 6 is a schematic representation of a fourth embodiment of a guide wire brake of the present invention showing the guide wire brake in an unclamped position.

A fourth embodiment of the guide wire brake of the present invention is shown in FIG. 6. The guide wire brake 400 includes a cylinder 410 having a cylindrical cavity 409. The cylinder 410 has oppositely disposed guide wire orifices 412 that are aligned perpendicularly with the longitudinal axis of the cylinder 410 to accommodate a guide wire 26 passing through the cylinder cavity 409 An inlet orifice 414 and an outlet orifice 416 are similarly provided in the cylinder 410. The inlet orifice 414 and the outlet orifice 416 are oppositely disposed above the guide wire orifices 412. A brake bypass assembly 430 is slidably disposed within the cylindrical cavity 409. A first brake shoe 436 is disposed within the cylinder cavity 409, below the guide wire 26. A shaft 434 having a knob 432 on its outer end extends axially through the outer cylinder 410 through an orifice 413, and connects to the first brake shoe 436, such that the first brake shoe 436 can be moved axially within the cylindrical cavity 409 by moving the knob 432 axially. A spring 438 biases the first brake shoe 436 to a first position wherein the first brake shoe 436 is adjacent the guide wire 26. By pulling downward on the knob 432, the first brake shoe 436 can be moved to a second position disposed away from the guide wire 26.

An inner cylinder 450 is rotatably disposed within the cylinder cavity 409, wherein at least the portion of the inner cylinder 450 that is adjacent inlet orifice 414 and outlet orifice 416 has an outer diameter that is approximately equal to the inner diameter of the cylinder cavity 409. The inner cylinder 450 has a transverse flow channel 452 therethrough, located such that when inner cylinder 450 is properly oriented, the flow channel 452 fluidly connects the inlet orifice 414 and the outlet orifice 416. A second shaft 442 having a lever 440 connected on its outer end extends axially through the cylinder 410 through an orifice 411, and connects to the inner cylinder 450, such that the inner cylinder 450 can be rotated within the cylinder 410 by rotating the lever 440. A helical groove 454 is provided on the circumference of the inner cylinder 450, extending part way around the inner cylinder 450. The bottom of the inner cylinder 450 comprises a second brake shoe 456, that is disposed above the guide wire 26, opposite the first brake shoe 436.

As shown in FIG. 6, a pin 420 having a first end 422 extends through the cylinder 410 such that a first end 422 slidably engages the helical groove 454 and restricts the axial movement of the inner cylinder 450. Rotation of the inner cylinder 450 will cause the inner cylinder 450 to move axially within the cylinder cavity 409. The inner cylinder helical groove 454 and the channel 452 are oriented such that the inlet orifice 414 and the outlet orifice 416 are fluidly connected by the channel 452 when the lever 440 is in a first position. Additionally, the length of the inner cylinder 450 is selected such that as the lever 440 is moved to the first position, the second brake shoe 456 moves adjacent the first brake shoe 436 so that the first brake shoe 436 and the second brake shoe 456 clamp the guide wire 26. When the lever 440 is in a second position, as shown in FIG. 6, the inner cylinder 450 closes the inlet orifice 414 and the outlet orifice 416, and the second brake shoe 456 is moved away from the guide wire 26, whereby the guide wire 26 is unclamped.

It will be appreciated that the guide wire brake 400 may be disposed in series between a pressurized gas source (not shown) that can be fluidly connected to the inlet port 414 and a turbine (also not shown) that can be fluidly connected to the outlet port 416, whereby the guide wire brake 400 will engage the guide wire 26 prior to connecting the turbine to the pressurized gas source.

The guide wire brake 400 can be effectively bypassed by pulling on the knob 432 of the brake bypass assembly 430, whereby the first brake shoe 436 will be moved away from the second brake shoe 456. It will be appreciated that bypassing the guide wire brake 400 requires constant force be applied to the knob 432, and that upon release of the knob 432 the guide wire brake 400 will re-engage the guide wire 26.

The embodiments of the invention in which an exclusive property or privilege is claimed are defined as follows:

1. A brake for a guide wire comprising:
   a gas manifold having a first and second gas outlet port, wherein said first gas outlet port is connected to a pressure relief valve;
   a brake cylinder having a proximal end and a distal end, said proximal end fluidly connected to said second gas outlet port through a check valve wherein said check valve inhibits gas flow out of said cylinder, and said distal end having a brake collet support;
   a brake collet comprising a back portion that engages said brake collet support, and a tapered front portion having two generally parallel flat surfaces oppositely disposed about said guide wire and separated by a gap having a width greater than a diameter of said guide wire, said two surfaces being elastically displaceable towards each other whereby said two surfaces can clampingly engage said guide wire;
   a piston slidable disposed within said cylinder comprising a collet engagement orifice whereby slidably urging said collet engagement orifice against said tapered front portion of said collet will cause said collet to clampingly engage said guide wire;
   a spring disposed within said cylinder biasing said piston toward said proximal end of said cylinder;
   whereby when sufficient gas pressure is provided to said manifold, said piston will move toward said distal end of said cylinder, and said collect engagement orifice will slidably engage said tapered front portion of said collet.

2. The guide wire brake of claim 1 further comprising an O-ring to form a seal between said piston and said cylinder.

3. The guide wire brake of claim 1 further comprising a valve for bypassing said brake cylinder whereby pressurized gas can be provided to said manifold without engaging said guide wire brake.

4. The guide wire brake of claim 3 wherein said valve is springedly biased in an open position whereby said guide wire brake can be bypassed only by applying continuous pressure to said valve.

5. The guide wire brake of claim 1 wherein said cylinder and said piston further comprise axial holes therethrough that are larger than said diameter of said guide wire.

6. A brake for a guide wire comprising:
   a guide wire engagement mechanism disposed within a brake cylinder that will engage said guide wire when said brake cylinder is connected to a compressed gas source and to a compressed-gas driven prime mover; and
   means for delaying the flow of said compressed gas to said prime mover whereby said guide wire engagement mechanism will engage said guide wire prior to the start-up of said prime mover.

7. The brake for guide wire of claim 6, wherein the means for delaying comprises a pressure relief valve disposed in series with the prime mover.

8. A guide wire brake for use with an atherectomy device that is rotated by a prime mover, comprising:
   a brake collet surrounding the guide wire that is selectively compressible around a guide wire;
   a piston having a collet engaging surface that compresses the collet around the guide wire;
   wherein said piston is adapted and arranged to engage the collet before the prime mover rotates the atherectomy device.

9. The guide wire brake of claim 8, further comprising a pressure release valve disposed in line with the prime mover, wherein the pressure relief valve requires a greater pressure to open and deliver gas to the prime mover than the pressure required to force the piston into the brake collet.

10. The guide wire brake of claim 8, wherein said guide wire brake is disposed in series with the prime mover, the guide wire brake having an air passage that supplies gas to the prime mover after the piston engages the brake collet.

* * * * *

UNITED STATES PATENT AND TRADEMARK OFFICE
CERTIFICATE OF CORRECTION

PATENT NO. : 6,503,227 B1
DATED : January 7, 2003
INVENTOR(S) : Z. Guo et al.

It is certified that error appears in the above-identified patent and that said Letters Patent is hereby corrected as shown below:

Column 9,
Line 55, "piston slidable" should read -- piston slidably --

Column 10,
Lines 2 and 41, "guide wire;" should read -- guide wire; and --
Line 35, "claim 6," should read -- claim 6 --
Lines 47 and 52, "claim 8," should read -- claim 8 --

Signed and Sealed this

Seventeenth Day of June, 2003

JAMES E. ROGAN
*Director of the United States Patent and Trademark Office*